(12) United States Patent
Bille

(10) Patent No.: US 6,451,006 B1
(45) Date of Patent: Sep. 17, 2002

(54) METHOD FOR SEPARATING LAMELLAE

(75) Inventor: Josef Bille, Heidelberg (DE)

(73) Assignee: 20/10 Perfect Vision Optische Geraete GmbH, Heidelberg (DE)

( * ) Notice: Subject to any disclaimer, the term of this patent is extended or adjusted under 35 U.S.C. 154(b) by 89 days.

(21) Appl. No.: 09/783,665

(22) Filed: Feb. 14, 2001

(51) Int. Cl.⁷ .................................................. A61F 9/01
(52) U.S. Cl. ............................................ 606/5; 606/12
(58) Field of Search ..................... 606/4, 5, 12; 128/898

(56) References Cited

U.S. PATENT DOCUMENTS

| | | |
|---|---|---|
| 4,669,466 A | 6/1987 | L'Esperance |
| 4,732,148 A | 3/1988 | L'Esperance |
| 4,770,172 A | 9/1988 | L'Esperance |
| 4,773,414 A | 9/1988 | L'Esperance |
| 4,887,592 A | 12/1989 | Loertscher |
| 5,062,702 A | 11/1991 | Bille |
| 5,984,916 A * | 11/1999 | Lai .............................. 606/11 |
| 6,050,687 A | 4/2000 | Bille |
| 6,110,166 A * | 8/2000 | Juhasz ........................... 606/5 |

* cited by examiner

Primary Examiner—Andrew M. Dolinar
(74) Attorney, Agent, or Firm—Nydegger & Associates

(57) ABSTRACT

A method for separating lamellae in the stroma of an eye includes establishing a focal depth that will be located in relatively weaker tissue at an interface layer between lamellae in the stroma. A laser beam can then be focused to photoablate stromal tissue and create a photoablative response thereto. This photoablative response is then compared to a reference value using wavefront analysis techniques to determine an effective minimum energy level for the laser beam. Maintenance of a proper focal depth can be periodically verified by maintaining a birefringent reference using an ellipsometer. Once the lamellae are separated, a flap of corneal tissue can be created that can be lifted to expose underlying stromal tissue for further surgical photoablation.

20 Claims, 2 Drawing Sheets

METHOD FOR SEPARATING LAMELLAE

FIELD OF THE INVENTION

The present invention pertains generally to ophthalmic laser surgery procedures. More particularly, the present invention pertains to laser surgical procedures which are performed to reshape or restructure the cornea of an eye by using photoablation techniques to remove stromal tissue. The present invention is particularly, but not exclusively, useful as a method and system for creating a flap in the cornea of an eye that can be moved or lifted to expose stromal tissue for photoablation.

BACKGROUND OF THE INVENTION

Within the past number of years, the so-called LASIK procedure has been used successfully to correct vision difficulties for a significantly large number of patients. In overview, a LASIK procedure is used to reshape or restructure the cornea of an eye in order to change its refractive properties. The object is to thereby minimize optical aberrations and to improve a patient's vision by altering the corneal shape.

As is well known to those skilled in the art, a LASIK procedure involves the removal of stromal tissue by photoablation. For a typical LASIK procedure, this photoablation is accomplished using an "excimer" laser. Excimer lasers, however, are most effective when they are used to superficially photoablate tissue. Accordingly, when using an excimer laser for the photoablation of tissue, it is necessary to somehow expose the target tissue that is to be photoablated. In the case of a LASIK procedure, it has been the practice to mechanically access the target tissue. Heretofore, this has involved the creation of a corneal flap which can be moved, or lifted, to expose the target tissue. The "excimer" laser is then used to photoablate the exposed stromal tissue. After the photoablation of tissue is accomplished, as desired the flap can be repositioned over the stroma. A major benefit of this so-called "Flap and Zap" procedure is that trauma to the epithelial layer at the anterior surface of the cornea is minimized. Trauma to the stroma under the epithelial layer, however, may still be significant.

A general knowledge of the anatomy of the cornea of an eye is helpful for appreciating the problems that must be confronted whenever a corneal flap is created. More specifically, the cornea comprises various layers of tissue which are structurally distinct. In order, going in a posterior direction from outside the eye toward the inside of the eye, the various layers in a cornea are: an epithelial layer, Bowman's membrane, the stroma, Decimet's membrane, and an endothelial layer. Of these various structures, the stroma is the most extensive and is generally around four hundred microns thick.

In detail, the stroma of the eye is comprised of around two hundred identifiable and distinguishable layers of lamella. Each of these layers of lamella in the stroma is generally dome-shaped, like the cornea itself, and they each extend across a circular area having a diameter of approximately six millimeters. Unlike the layer that a particular lamella is in, each lamella extends through a shorter distance of only about one tenth to one and one half millimeters. Thus, each layer includes several lamellae. Importantly, each lamella includes many fibrils which, within the lamella, are substantially parallel to each other. The fibrils in one lamella, however, are not generally parallel to the fibrils in other lamellae. This is so between lamellae in the same layer, as well as between lamellae in different layers. Finally, it is to be noted that, in a direction perpendicular to the layer, the individual lamella are only about two microns thick.

Within the general structure described above, there are at least three important factors concerning the stroma that are of interest insofar as the creation of a corneal flap is concerned. The first of these factors is structural, and it is of interest here because there is a significant anisotropy in the stroma. Specifically, the strength of tissue within a lamella is approximately fifty times the strength that is provided by the adhesive tissue that holds the layers of lamella together. Thus, much less energy is required to separate one layer of lamella from another layer (i.e. peel them apart), than would be required to cut through a lamella. The second factor is somewhat related to the first, and involves the stromal tissue response to photoablation. Specifically, for a given energy level in a photoablative laser beam, the bubble that is created by photoablation in the stronger lamella tissue will be noticeably smaller than a bubble created between layers of lamellae. The third factor is optical, and it is of interest here because there is a change in the refractive index of the stroma between successive layers of lamellae. This is due to differences in the orientations of fibrils in the respective lamella. When consideration is given to using a laser beam for the purpose of creating a corneal flap in a LASIK procedure, these factors can be significant.

In light of the above, it is an object of the present invention to provide a method for using a laser beam to separate lamella in the stroma of an eye which minimizes the heating of the stromal tissue. Another object of the present invention is to provide a method for using a laser beam to separate lamellae in the stroma of an eye that can be accomplished quickly in order to minimize the time a patient must fixate. Still another object of the present invention is to provide a method for separating lamellae in the stroma that avoids excessive trauma to the stromal tissue in the cornea. Yet another object of the present invention is to provide a method for separating lamellae in the stroma that is easy to perform and is comparatively cost effective.

SUMMARY OF THE PREFERRED EMBODIMENTS

In accordance with the present invention, a method for separating lamellae in the stroma of an eye requires focusing a laser beam between layers of the lamellae and photoablating tissue at the interface between these layers. This involves first locating a start point in the stroma. Preferably, this start point will be at a distance into the stroma that is approximately one hundred and eighty microns from the anterior surface of the cornea. As contemplated by the present invention, the anterior surface of the cornea can be identified using a wavefront sensor.

Once the start point is located, tissue at the start point is photoablated to create a bubble. The size of this bubble is then measured and compared with a reference to determine whether the bubble was created within a lamella or between layers of lamellae. If the bubble is created inside a lamella, subsequent bubbles can be created at different points in the stroma until the resultant bubble size indicates that photoablation is occurring between layers of lamellae. An ellipsometer is then used to detect a birefringent condition in the stroma between these layers of lamellae. Specifically, this birefringent condition will result from a change in the orientation of fibrils in the respective lamella, and will be indicative of the interface between layers of lamellae in the stroma. Further, it happens that from layer to layer of lamellae there will be a birefringent change that is manifested as a change in phase of about one half degree. Recall, the thickness of the lamellae is around two microns. The importance of all this is that the detection of a birefringent change will indicate a change from one layer of lamellae to another. Thus, it can be used to establish and maintain a focal depth in the stroma, The photoablation of tissue along the interface between layers of lamellae in the stroma begins by focusing the laser beam to a focal point at the established focal depth in the stroma. Initially, the laser beam is set to operate at an energy level that is slightly above the threshold for photoablation of stromal tissue (i.e. above approximately one and one half microjoules for a ten micron diameter spot size). For example, the initial energy level that can be used for the laser beam may be around five microjoules for a ten micron diameter spot. In any event, whenever the laser beam is activated, there will be a photoablative response from the tissue that results from the particular energy level that is being used. Importantly, this photoablative response will vary according to the energy level of the laser beam, as well as the nature of the tissue that is being photoablated.

As intended for the present invention, the photoablative response is measured as the diameter of the gas bubble that is created in the stromal tissue during photoablation. This photoablative response is then compared with the reference value mentioned above to determine whether the initial energy level is sufficient for further operation. For the purposes of the present invention, this reference value is chosen to correspond to a hypothetical gas bubble in the stroma that, as a result of photoablation, would have a diameter of approximately fifteen microns. Depending on the difference between the photoablative response and the reference value, the energy level of the laser beam will either be held constant, or it will be changed. For the present invention, the change in energy level will be between a relatively low energy level (e.g. approximately five microjoules per ten micron diameter spot size) and a relatively high energy level (e.g. approximately fifteen microjoules per ten micron diameter spot size).

A condition wherein the photoablative response is greater than the reference value is indicative that the photoablation of tissue is occurring in the weaker tissue that is located at the interface between layers of lamella, rather than inside the lamella. Accordingly, further photoablation is accomplished by maintaining the initial energy level of the laser beam at the relatively lower energy level, and moving its focal point at the focal depth between the layers of lamellae. As this is being done, the ellipsometer can be used periodically to ensure the photoablation is being done at the same interface between lamellae. This continues as long as this condition persists. On the other hand, when the photoablative response becomes less than the reference value, the indication is that the focal point is no longer located between layers of lamellae. Thus, the energy level needs to be increased to a higher energy level. Also, the focal point needs to be moved until the photoablative response is substantially greater than the reference value. At this point, i.e. when the photoablative response becomes substantially greater than the reference value, the indication is that the focal point is again between layers of lamella. The energy level of the laser beam is then returned to its former lower value. Also, if desired, the focal depth can be verified by the ellipsometer and adjusted as necessary.

In the operation of the present invention, the energy level of the laser beam is altered in the above manner to follow the interface between lamella, and it is guided to create a flap from the corneal tissue. Specifically, the focal spot of the laser beam is moved within a boundary that can be generally defined by a first edge and a second edge. More specifically, to create the flap, the first edge should be a substantially straight line between a first point and a second point. The second edge can then be a curved line between the first point and the second point with the curved line having a radius of curvature around the optical axis of the eye of about four and one half millimeters. Further, this curved line should be centered approximately on the optical axis of the eye and extend through an arc of about two hundred and seventy degrees.

BRIEF DESCRIPTION OF THE DRAWINGS

The novel features of this invention, as well as the invention itself, both as to its structure and its operation, will be best understood from the accompanying drawings, taken in conjunction with the accompanying description, in which similar reference characters refer to similar parts, and in which.

DESCRIPTION OF THE PREFERRED EMBODIMENT

Figure 1:
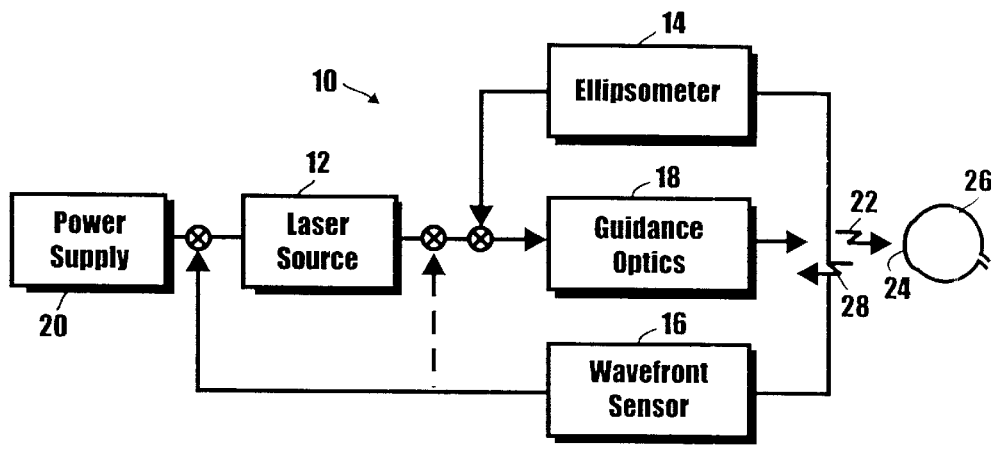
FIG. 1 is a schematic diagram, in a closed-loop feedback control format, showing the operative components of an apparatus that is useful for performing the methods of the present invention.

Referring initially to FIG. 1, an apparatus for use in performing the methods of the present invention is shown schematically in a control loop format and is generally designated 10. As shown, the apparatus 10 includes a laser source 12 which, preferably, is capable of generating a continuous train of ultra-short pulses, with each pulse having a pulse duration of approximately one picosecond. Specifically, it is necessary that each pulse have an energy level that is above the threshold necessary for the photoablation of stromal tissue (i.e. above approximately one and one half microjoules per ten micron diameter spot size). The apparatus 10 also includes an ellipsometer 14 that is capable of determining the birefringent properties within stromal tissue. For the purposes of the present invention, an ellipsometer of the type disclosed and claimed in U.S. Pat. No. 5,822,035, which issued to Bille for an invention entitled "Ellipsometer." Further, FIG. 1 shows that the apparatus 10 includes a wavefront sensor 16, such as a Hartmann-Shack sensor, which is capable of modeling a wavefront. Additionally, the apparatus 10 includes guidance optics 18 that are capable of steering and focusing a laser beam onto predetermined focal points. A power unit 20 is also provided. In combination, these components cooperate with each other to generate a laser beam 22 that is directed to a focal point in the cornea 24 of an eye 26 with a predetermined energy level. Control over this operation, to include the location of the focal point and its energy level, is made possible by using the ellipsometer 14 and the wavefront sensor 16 to monitor reflected light 28 as it is reflected from the cornea 24.

Figure 3:
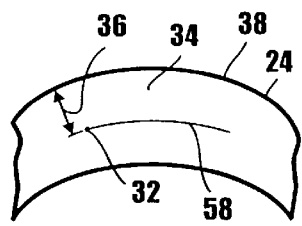
FIG. 3 is a cross sectional view of the cornea of an eye.
Figure 2:
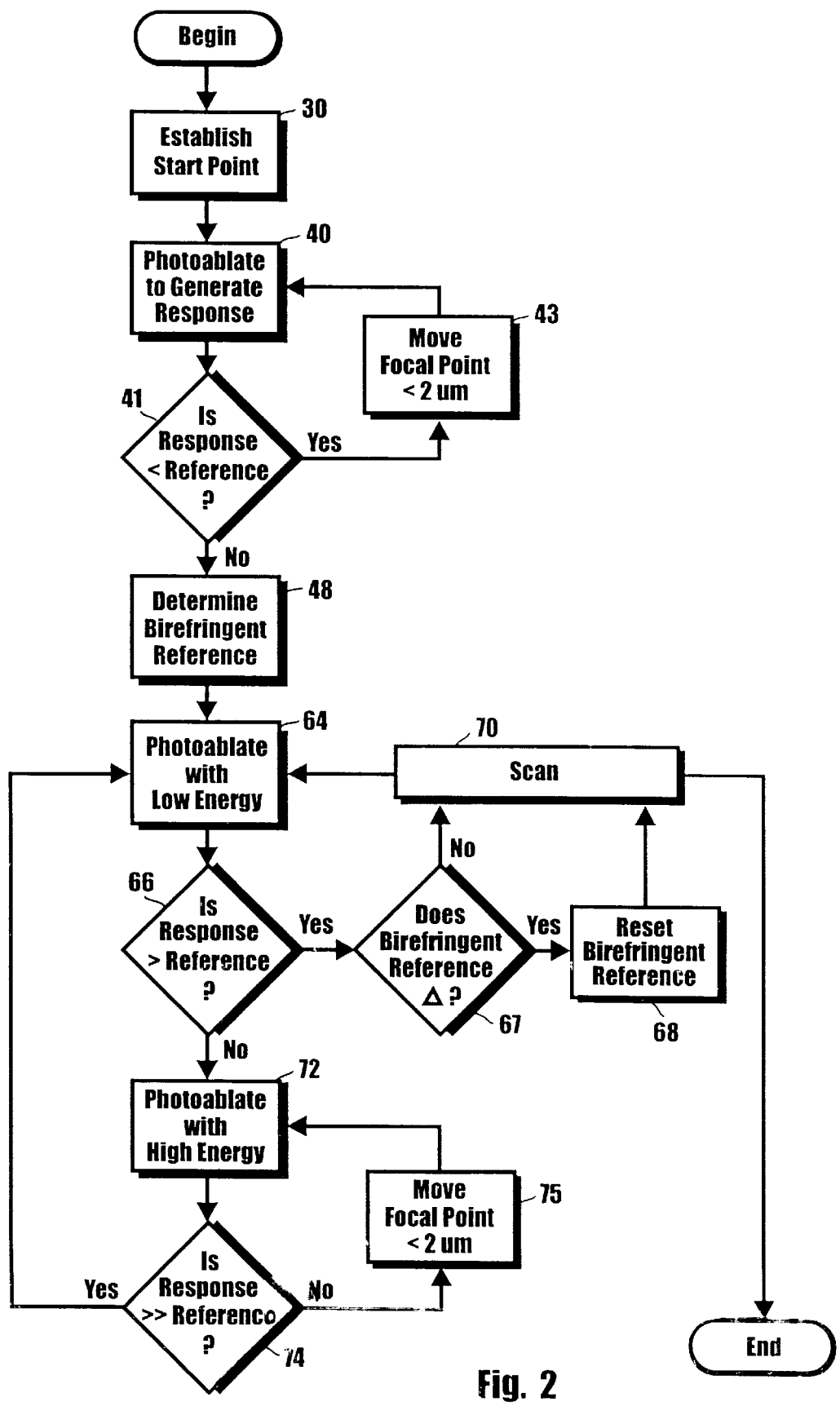
FIG. 2 is a logic flow chart of the sequential steps to be accomplished in accordance with the methods of the present invention.

Referring now to FIG. 2, it will be seen that in the operation of apparatus 10, the performance of the methods of the present invention begins by establishing a start point (action block 30). In FIG. 3 it will be seen that this start point 32 is established in the stroma 34 of cornea 24. Specifically, the start point 32 is established at a distance 36 that is measured from the anterior surface 38 of the cornea 24 in a direction that is substantially perpendicular to the anterior surface 38. As intended for the apparatus 10, the exact location of the anterior surface 38 can be determined using the wavefront sensor 16, and the distance 36 can then be arbitrarily chosen to be around about one hundred and eighty microns from the anterior surface 38.

Figure 4:
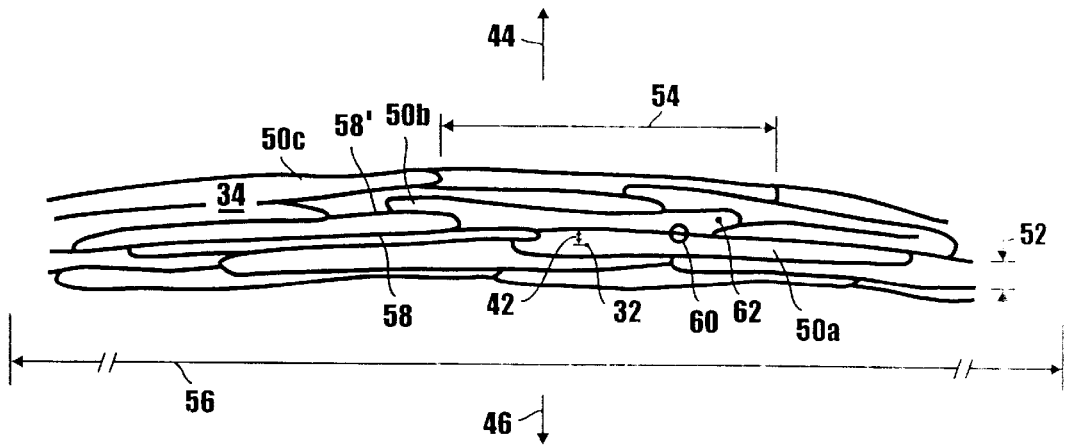
FIG. 4 is a cross sectional view of layers of lamella in the cornea of an eye.

Once a start point 32 has been established in the stroma 34, action block 40 in FIG. 2 indicates that the next step in the methods of the present invention is to photoablate tissue at the start point 32 to create a response (i.e. a bubble in the stromal tissue). As indicated by inquiry block 41, this response is then compared with a reference (e.g. 15 $\mu$m). If the response is less than the reference, action block 43 indicates the focal point should be moved from the start point 32 through a distance 42 (FIG. 4). This distance 42 will preferably be taken in an anterior direction (indicated by the arrow 44 in FIG. 4) and will, most likely, be less than two microns. It will be appreciated, however, that in some cases this distance 42 may be taken in a posterior direction (indicated by arrow 46 in FIG. 4). In either case, as this movement from the start point 32 is being accomplished, the inquiry block 41 in FIG. 2 indicates that when the response becomes greater than the reference, reflected light 28 from cornea 24 can be monitored by the ellipsometer 14 to determine a birefringent reference (action block 48). It happens that this birefringent reference can be determined due to a variation in the orientation of tissue in the stroma 34 and will, perhaps, be best understood by reference to FIG. 4.

In FIG. 4, a portion of the stroma 34 in the cornea 24 of the eye 26 is shown to include a plurality of lamellae 50, of which the lamellae 50a, 50b and 50c are only exemplary. Dimensionally, each of the lamellae 50 in the stroma 34 have a depth 52 that is approximately two microns, and a width 54 that is between approximately one tenth and one and one half millimeters. Thus, the lamellae 50 each have a very thin disk shape. Anatomically, the lamella 50 lie on top of each other in layers that extend across the cornea 24 through a distance 56 that is approximately nine millimeters. As shown in FIG. 4, the individual lamella 50 overlap to some extent and are somewhat randomly arranged. Nevertheless, they create many interface layers that, in general, are substantially parallel to each other and extend all the way across the cornea 24. The interface layer 58 shown in FIG. 4 is only exemplary of the many interface layers in the cornea 24.

For the purposes of the present invention, an interface layer 58 is important in two aspects. First, the birefringent properties of stromal tissue in the lamella 50 change at the interface layer 58. Recall, from the disclosure above, this change in birefringent properties is due to changes in the orientation of fibrils (not shown) in the lamella 50. Second, the stromal tissue along the interface layer 58 is weaker than stromal tissue inside the lamella 50. Accordingly, the stromal tissue along the interface layer 58 can be effectively photoablated at lower energy levels.

It happens that whenever stromal tissue is photoablated, a bubble is formed in the stroma 34. For a given type of tissue, the size of the bubble that is formed will be a function of the energy level in the laser beam 22. In this case, the higher the energy level, the larger the bubble. Further, for a given energy level, the size of the bubble that is formed will be a function of the type of tissue. In this case, with the same energy level, the stronger tissue will yield a smaller bubble and the weaker tissue will yield a larger bubble. With this in mind, consider the bubbles 60 and 62 shown (not to scale) in FIG. 4 that would be formed using a same energy level in the laser beam 22. The larger bubble 60 is shown generally in weaker tissue at the interface layer 58 between the lamella 50a and 50b. On the other hand, the smaller bubble 62 is shown in stronger tissue inside the lamella 50b. Fortunately, as used for the present invention, the respective sizes of the bubbles 60 and 62 will serve as photoablative responses that can be measured by the wavefront sensor 16 using relatively well known wavefront techniques. Accordingly, the photoablative response of a bubble 60 or bubble 62 can be compared with a reference value, and the energy level of the laser beam 22 can be altered as desired.

Returning now to FIG. 2, and in light of the above discussion with reference to FIG. 4, it will be appreciated that the combined functions of inquiry block 41 and action block 48 is to find the interface layer 58. This is accomplished whenever the ellipsometer 14 detects a birefringent change. It will happen that this birefringent change will be on the order of plus or minus one half degree. Importantly, finding the interface layer 58 will fix a focal depth for the laser beam 22 that will be a combination of the distances 36 and 42. The apparatus 10 can then begin to photoablate stromal tissue (action block 64).

Action block 64 in FIG. 2 indicates that, at least initially, the apparatus 10 will photoablate stromal tissue at a relatively low energy level, e.g. approximately five microjoules per ten micron spot size. As indicated above, if photoablation begins at this energy level in the interface layer 58 as intended, a relatively large bubble 60 will result. In any event, as indicated by the inquiry block 66, the resultant bubble (photoablative response) will be compared with a reference value to determine whether photoablation at this energy level should continue (inquiry block 66). For the present invention, the reference value will correspond to a hypothetical bubble in stromal tissue (not shown) which would have a diameter of approximately fifteen microns. If the resultant bubble in the stroma 34 has a photoablative response that is greater than the reference value, it is indicative of the fact that weaker tissue in the interface layer 58 is being photoablated. In this case, the inquiry block 67 may be selectively used to determine whether the birefringent reference has changed. Such a change would be on the order of one half a degree and would indicate that another interface 58' was being photoaltered. If so, action block 68 indicates the birefringent reference can be reset to reestablish on the desired interface 58. In either case, the action block 70 in FIG. 2 indicates that the guidance optics 18 should continue to scan the laser beam 22 through the interface layer 58. As this is being done, the interaction of blocks 64, 66, 67 and 68 in FIG. 2 indicate that a photoablative response is continuously being monitored by the wavefront sensor 16.

Whenever the photoablative response falls below the reference value, such as would happen when photoablation is occurring within a lamella 50 (e.g. bubble 62), action block 72 indicates that the energy level in the laser beam 22 should be increased to a higher energy level. Again, the photoablative response is monitored by the wavefront sensor 16. Due to the higher energy level being used, when the laser beam 22 is next focused onto the interface layer 58, the photoablative response will most likely be much greater than the reference value. In any event, inquiry block 74 and action block 75 indicates that the laser beam 22 will continue to move and photoablate tissue until the photoablative response is considerably greater than the reference value. When this happens, depending on the desires of the operator, the methods of the present invention indicate that the laser beam 22 can continue operation at the relatively lower energy level (action block 64). In either case, blocks 66, 67, 68 and 70 indicate that the photoablation of stromal tissue will continue until the procedure is ended. Specifically, the procedure is ended when an interface layer 58 having a predetermined dimension has been created.

Figure 5:
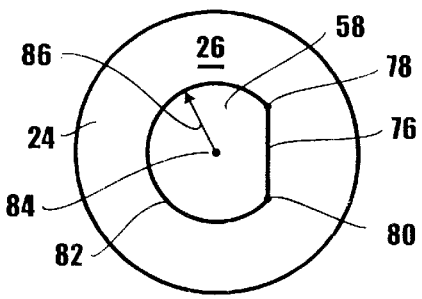
FIG. 5 is a plan view of the cornea of an eye.

It is the purpose of the present invention to create a flap of corneal tissue that can be lifted easily from the eye to expose stromal tissue under the flap to further surgical photoablation. Accordingly, the present invention is directed toward the photoablation of weaker tissue along an interface layer 58 between lamella 50 and to, thereby, use less laser energy. The extent of this photoablation will be best appreciated with reference to FIG. 5. In FIG. 5, a substantially straight edge 76 is shown between a point 78 and a point 80. Also, a substantially curved edge 82 is shown connecting the point 78 to the point 80. More specifically, the curved edge 82 is generally centered on the optical axis 84 of the eye 26 and has a radius of curvature 86 that defines the edge 82. As shown, the curved edge 82 will extend through approximately two hundred and seventy degrees. Effectively the desired corneal flap will be created between the straight edge 76 and the curved edge 82. Consequently, by photoablating tissue between the anterior surface 38 of the cornea 24 and the curved edge 82, a flap of corneal tissue can be lifted from the interface layer 58 to expose stromal tissue under the flap for further photoablation.

While the particular Method for Separating Lamellae as herein shown and disclosed in detail is fully capable of obtaining the objects and providing the advantages herein before stated, it is to be understood that it is merely illustrative of the presently preferred embodiments of the invention and that no limitations are intended to the details of construction or design herein shown other than as described in the appended claims.

What is claimed is:

1. A method for separating lamellae in the stroma of an eye which comprises the steps of:
    focusing a laser beam to a focal point in the stroma to photoablate stromal tissue and create a photoablative response thereto, said photoablative response being indicative of a diameter of a gas bubble created in the stroma during photoablation of the stromal tissue;
    comparing said photoablative response to a reference value;
    moving said laser beam to another focal point to perform said focusing step and to thereafter perform said comparing step;
    alternating energy in said laser beam from a first energy level to a second energy level when said photoablative response is less than said reference value and from said second energy level to said first energy level when said photoablative response is greater than said reference value; and
    detecting a birefringent reference in the stroma when said first energy level is used, said birefringent reference being indicative of an interface between layers of lamellae.

2. A method as recited in claim 1 wherein said first energy level is lower than said second energy level.

3. A method as recited in claim 2 further comprising the step of repeating said detecting step to reset said birefringent reference whenever said energy level is alternated from said second energy level to said first energy level.

4. A method as recited in claim 3 wherein said birefringent reference is reset whenever there is a change in the birefringent reference greater than approximately one half degree.

5. A method as recited in claim 1 wherein said moving step is accomplished within a boundary to create a flap of corneal tissue, said boundary having a first edge and a second edge with said first edge being a substantially straight line between a first point and a second point and said second edge being a curved line between said first point and said second point with said curved line having a radius of curvature around the optical axis of the eye of about four and one half millimeters and said curved line extending through an arc of about two hundred and seventy degrees.

6. A method as recited in claim 1 wherein a start point is measured into the stroma at a distance from the anterior surface of the eye and said focusing step is first performed at said start point.

7. A method as recited in claim 5 wherein said distance is approximately equal to one hundred and eighty microns.

8. A method as recited in claim 1 wherein said reference value is indicative of a gas bubble in the stroma having a diameter of approximately fifteen microns.

9. A method for separating lamellae in the stroma of an eye which comprises the steps of:
    finding an interface layer between lamella in the stroma;
    focusing a laser beam to a focal point at the interface layer to photoablate stromal tissue and create a photoablative response thereto, said photoablative response being indicative of a diameter of a gas bubble created in the stroma during photoablation of the stromal tissue;
    comparing said photoablative response to a reference value;
    moving said focal point of said laser beam to perform said focusing step and to thereafter perform said comparing step; and
    alternating energy in said laser beam from a first energy level to a second energy level when said photoablative response is less than said reference value and from said second energy level to said first energy level when said photoablative response is greater than said reference value.

10. A method as recited in claim 9 wherein said first energy level is lower than said second energy level.

11. A method as recited in claim 10 wherein said finding step comprises the steps of:
    identifying the anterior surface of the eye;
    locating a start point in the stroma at a distance from the anterior surface;
    initially performing said focusing step at said start point; and
    detecting a birefringent reference in the stroma when said first energy level is used, said birefringent reference being indicative of an interface between layers of lamellae.

12. A method as recited in claim 11 further comprising the step of repeating said detecting step whenever said energy level is alternated from said second energy level to said first energy level.

13. A method as recited in claim 12 wherein said distance is approximately equal to one hundred and eighty microns, and wherein said reference value is indicative of a gas bubble in the stroma having a diameter of approximately fifteen microns.

14. A method as recited in claim 9 wherein said moving step is accomplished within a boundary to create a flap of corneal tissue, said boundary having a first edge and a second edge with said first edge being a substantially straight line between a first point and a second point and said second edge being a curved line between said first point and said second point with said curved line having a radius of curvature around the optical axis of the eye of about four and one half millimeters and said curved line extending through an arc of about two hundred and seventy degrees.

15. An apparatus for separating lamellae in the stroma of an eye which comprises:

means for finding a focal depth in the stroma;

means for sequentially focusing a laser beam to a plurality of focal points in the stroma to photoablate stromal tissue at said focal depth to separate the lamellae and create a photoablative response thereto, said photoablative response being indicative of a diameter of a gas bubble created in the stroma during photoablation of the stromal tissue; and means for alternating from a first energy level to a second energy level when said photoablative response is less than a reference value, and from said second energy level to said first energy level when said photoablative response is greater than said reference value.

16. An apparatus as recited in claim 15 wherein said finding means comprises:

a wavefront sensor for identifying the anterior surface of the eye;

a measuring means for locating a start point in the stroma at a distance from the anterior surface, said distance being approximately one hundred and eighty microns; and an ellipsometer for detecting a birefringent change in the stroma within approximately two microns from said start point to establish said focal depth.

17. An apparatus as recited in claim 16 further comprising a wavefront sensor for detecting said photoablative response.

18. An apparatus as recited in claim 17 wherein said first energy level is lower than said second energy level.

19. An apparatus as recited in claim 18 wherein a polarization change due to said birefringence is approximately equal to one half degree, and wherein said reference value is indicative of a gas bubble in the stroma having a diameter of approximately fifteen microns.

20. An apparatus as recited in claim 19 wherein photoablation of stromal tissue is accomplished within a boundary to create a flap of corneal tissue, said boundary having a first edge and a second edge with said first edge being a substantially straight line between a first point and a second point and said second edge being a curved line between said first point and said second point with said curved line having a radius of curvature around the optical axis of the eye of about four and one half millimeters and said curved line extends through an arc of about two hundred and seventy degrees.

\* \* \* \* \*